United States Patent
Pieters et al.

(10) Patent No.: US 9,901,609 B2
(45) Date of Patent: Feb. 27, 2018

(54) MEDICINAL PLANT EXTRACT

(71) Applicants: UNIVERSITY OF ANTWERP, Antwerp (BE); AVICENNA DEVELOPMENT, Hofstade (BE)

(72) Inventors: Luc Pieters, Antwerp (BE); Sandra Apers, Puurs (BE); Mart Theunis, Deurne (BE); Mark Vaeck, Hofstade (BE); Khalil El Mazouari, Vinderhoute (BE); Yahia Cherrah, Harhoura (MA)

(73) Assignees: AVICENNA DEVELOPMENT, Hofstade (BE); UNIVERSITY OF ANTWERP, Antwerp (BE)

( * ) Notice: Subject to any disclaimer, the term of this patent is extended or adjusted under 35 U.S.C. 154(b) by 114 days.

(21) Appl. No.: 15/026,626

(22) PCT Filed: Oct. 14, 2014

(86) PCT No.: PCT/EP2014/071987
§ 371 (c)(1),
(2) Date: Apr. 1, 2016

(87) PCT Pub. No.: WO2015/055633
PCT Pub. Date: Apr. 23, 2015

(65) Prior Publication Data
US 2016/0213726 A1 Jul. 28, 2016

(30) Foreign Application Priority Data
Oct. 16, 2013 (EP) .................................. 13188906

(51) Int. Cl.
*A61K 36/36* (2006.01)
*A61K 31/704* (2006.01)
*A61K 31/7048* (2006.01)

(52) U.S. Cl.
CPC ............ *A61K 36/36* (2013.01); *A61K 31/704* (2013.01); *A61K 31/7048* (2013.01)

(58) Field of Classification Search
CPC .................................................. A61K 36/00
See application file for complete search history.

(56) References Cited

PUBLICATIONS

Atmani, Extract from Herniaria hirsuta coats calcium oxalate monohydrate crystals and blocks their adhesion to renal epithelial cells. The Journal of urology, (Oct. 2004) vol. 172, No. 4 Pt 1, pp. 1510-1514.*
PCT International Search Report and Written Opinion dated Dec. 9, 2014 for PCT International Patent Application No. PCT/EP2014/071987, 12 pages.
Notification of Transmittal of the International Preliminary Report on Patentability dated Jan. 19, 2016 for PCT International Patent Application No. PCT/EP2014/071987, 10 pages.
Atmani F et al., entitled "Effect of aqueous extract from *Herniaria hirsuta* L. on experimentally nephrolithiasic rats," Journal of Ethnopharmacology, vol. 95, No. 1, Nov. 1, 2004, pp. 87-93.
Atmani F et al., entitled "Extract from herniaria hirsuta coats calcium oxalate monohydrate crystals and blocks their adhesion to renal epithelial cells," The Journal of Urology, vol. 172, No. 4, Oct. 1, 2004, pp. 1510-1514.
Meiouet F et al., entitled "In vitro study of the litholytic effects of herbal extracts on cystine urinary calculi," Progres En Urologie, vol. 21, No. 1, Jan. 1, 2011, pp. 40-47.
Grases F et al., entitled "Effect of Herniara hirsute and Agropyron repens on calcium oxalate urolithiasis risk in rats," Journal of Ethnopharmacology, 45, 1995, pp. 211-214.
Nagal A et al., entitled "Herbal resources with antiurolithiatic effects: A review," Indo Global Journal of Pharmaceutical Sciences, 2013; 3(1): 6-14.
Mbark A N et al., entitled "Monodesmosidic saponins from Herniaria hirsuta" Die Pharmazie, vol. 55, No. 9, Sep. 1, 2000, pp. 690-692.
Tamas M et al., entitled "The comparative phytochemical study of saponines, flavones and cumarines from *Herniaria glabra* L. and *H. Hirsuta* L. (Caryophilaceae)," Clujul Medical, 1977, vol. 50, No. 2, pp. 198-204.
Written Opinion dated Oct. 16, 2015 for PCT International Patent Application No. PCT/EP2014/071987, 6 pages.
Reply dated Aug. 14, 2015 to Written Opinion for PCT International Patent Application No. PCT/EP2014/071987, 8 pages.

* cited by examiner

*Primary Examiner* — Qiuwen Mi
(74) *Attorney, Agent, or Firm* — Amster, Rothstein & Ebenstein LLP

(57) ABSTRACT

The application relates to medicinal plant extracts and their use in the treatment of diseases, more particularly diseases caused by the presence of stones in ducts of the digestive system.

12 Claims, 2 Drawing Sheets

MEDICINAL PLANT EXTRACT

CROSS-REFERENCE TO RELATED APPLICATIONS

Figure 1:
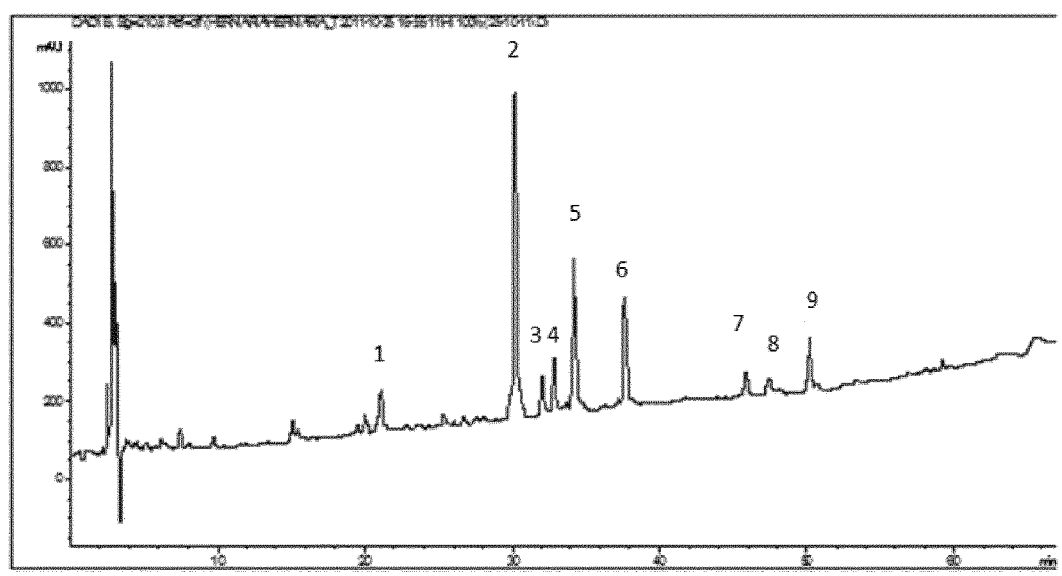

This application is a U.S. national stage entry under 35 U.S.C. § 371 of PCT International Patent Application No. PCT/EP2014/071987, filed Oct. 14, 2014, which claims priority to European Patent Application No. 13188906.5, filed Oct. 16, 2013, the contents of which are incorporated herein by reference in their entirety.

FIELD OF THE INVENTION

The application relates to medicinal plant extracts and their use in the treatment of diseases, more particularly diseases caused by the presence of stones in ducts of the digestive system.

BACKGROUND

The bile present in the gallbladder can harden into pieces of stone-like material which, when pushed out of the gallbladder can obstruct not only the cystic duct and the common bile duct but also neighbouring ducts such as the hepatic or pancreatic ducts. This can give rise to diseases such as cholelithiasis, choledocholithiasis, which may result in cholangitis, obstructive jaundice, and pancreatitis. Despite the frequency of these conditions the clinical management of stones identified in the bile ducts in the intestine is almost exclusively based on the removal of the bile duct through cholecystectomy.

Cholecystectomy, although an established procedure, still carries a small but existent complication rate, especially when performed in an acute setting. Some 20% of patients continue to suffer from pain after cholecystectomy, and symptomatic therapy with analgesia (non-steroidal anti-inflammatory drugs (NSAIDs), narcotic analgesics) is designated. Medical dissolution therapy with ursodeoxycholic acid (UDCA) is an alternative for patients experiencing moderate symptoms due to cholesterol gallstones. The main drawbacks of this treatment are the low efficacy, slowness in action and the possibility of stone recurrence.

Drugs influencing hepatic synthesis and/or secretion of cholesterol like statins, and/or intestinal absorption of cholesterol like ezetimibe might be able to influence the formation of cholesterol gallstones and promote the dissolution of gallstones, but this concept has not yet been proven in the clinic. Moreover, synthetic chemical drugs often have side effects.

*Herniaria hirsuta* L. (*Caryophyllaceae*), native to Eurasia and Northern Africa, is used in folk medicine for the treatment of lithiasis or as a diuretic (Atmani et al., 2004, Journal of Ethnopharmacology 139:728-738; Mbark et al., 2000, Die Pharmazie 55:690-692).

SUMMARY OF THE INVENTION

Provided herein are plant extracts, more particularly extracts of *Herniaria hirsuta*, which are particularly advantageous for use in the treatment of diseases associated with the presence of stones in the digestive system, more particularly in bile ducts such as the cystic duct. More particularly, the extracts provided herein are effective in the prevention and treatment of gallstones. Most particularly the extracts provided herein are shown to prevent the increase of bile cholesterol and thus prevent bile mud and gallstone formation. The extracts provided herein are thus of particular interest in the treatment of patients at high risk for developing diseases such as cholelithiasis. More particularly, it has been found that the administration of between 30 mg and 70 mg/kg body weight per day of a *Herniaria hirsuta* extract, more particularly, the administration of between 40 mg and 60 mg/kg body weight per day of a *Herniaria hirsuta* extract wherein the total amount of *Herniaria hirsuta* saponins is between 5% and 18%, and which in addition contains flavonoids, is particularly effective in the prevention and/or treatment of these diseases.

Accordingly, provided herein are *Herniaria hirsuta* extracts comprising one or more *Herniaria hirsuta* saponins and one or more *Herniaria hirsuta* flavonoids for use in the prevention and/or treatment of a disease associated with stones present in the duct of the digestive system, characterized in that the extract is administered at a dosage such that between 3.6 mg and 8.4 mg/kg bodyweight of *Herniaria hirsuta* saponins are administered per day.

In particular embodiments, the *Herniaria hirsuta* extracts envisaged herein are for use in the treatment and/or prevention of cholelithiasis or choledocholithiasis.

In particular embodiments, the *Herniaria hirsuta* extracts envisaged herein are for use in a method for lowering bile cholesterol.

It has further been found that the above-described advantageous effects can be optimally obtained with compositions which are standardized *Herniaria hirsuta* extracts.

It will be understood that depending on the concentration of the components in the extracts, different dosage forms can be determined by the skilled person for the methods described above.

In particular embodiments, the application further provides standardized *Herniaria hirsuta* extracts characterized in that they comprise one or more *Herniaria hirsuta* saponins and one or more *Herniaria hirsuta* flavanoids and the total amount of saponins is between 5% and 18%.

In particular embodiments, the standardized *Herniaria hirsuta* extracts envisaged herein are characterized in that the *Herniaria hirsuta* saponins comprised therein include one or more of hydroxymedicagenic acid heptaglycoside and medicagenic acid heptaglycoside.

In further particular embodiments, the standardized *Herniaria hirsuta* extracts envisaged herein are characterized in that they comprise the *Herniaria hirsuta* saponins hydroxymedicagenic acid heptaglycoside and medicagenic acid heptaglycoside.

In particular embodiments, the standardized *Herniaria hirsuta* extracts envisaged herein are characterized in that the *Herniaria hirsuta* flavonoids comprised therein include one or more of quercetine-3-O-(2-O-rhamnosyl)glucuronide, rutine and isorhamnetine-3-O-rutinoside.

In further particular embodiments, the standardized *Herniaria hirsuta* extracts envisaged herein are characterized in that they comprise the *Herniaria hirsuta* flavonoids quercetine-3-O-(2-O-rhamnosyl)glucuronide, rutine and isorhamnetine-3-O-rutinoside.

As detailed above, the application provides the standardized *Herniaria hirsuta* extracts as envisaged herein for use in methods for the prevention or/and treatment of a disease associated with stones present in the duct of the digestive system.

In particular embodiments, the standardized *Herniaria hirsuta* extracts envisaged herein are for use as described above, wherein said prevention and/or treatment comprises administration of said extract to a patient in need thereof at a dosage between 0.5 g extract/day and 10.0 g extract/day.

The present application further provides methods for producing extracts of *Herniaria hirsuta* and an analytical, validated method, which allow the generation of extracts having one or more of the properties as envisaged herein.

More particularly, the application envisages methods for producing standardized extract material of *Herniaria hirsuta*, characterized by the steps of contacting plant material of *Herniaria hirsuta*, with an extraction fluid so as to extract at least flavonoids and saponins therefrom; determining the amount of *Herniaria hirsuta* saponins in the extract so obtained; and obtaining therefrom an extract material wherein the total amount of *Herniaria hirsuta* saponins is between 5% and 18%.

In particular embodiments the extract material characterized by the specified amount of *Herniaria hirsuta* saponins is ensured by mixing different batches of *Herniaria hirsuta* extracts, or by mixing with one or more inert excipients (dilution).

The application further provides standardized *Herniaria hirsuta* extracts, obtainable by the methods described herein.

FIGURES

The following description of the figures of specific embodiments is merely exemplary in nature and is not intended to limit the present teachings, their application or uses.

FIG. 1: HPLC profile of a standardized *Herniaria hirsuta* extract as obtained using the validated method envisaged herein. The different peaks identified correspond to: 1 caffeic acid derivative, 2-6 flavonoids, 7-9 saponins.

Figure 2:
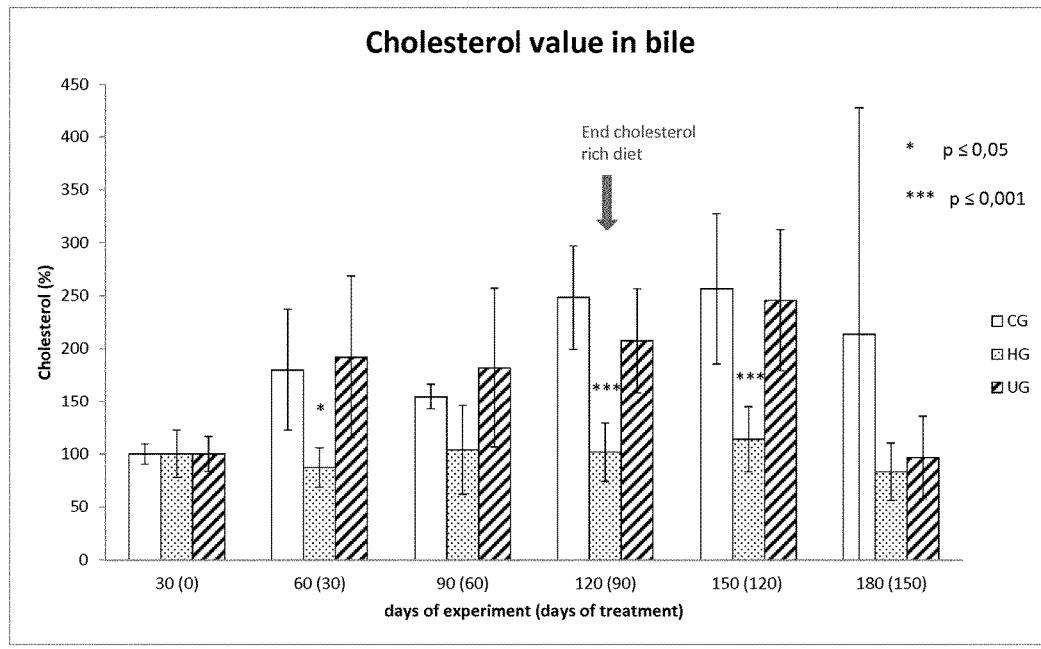
Figure 2:
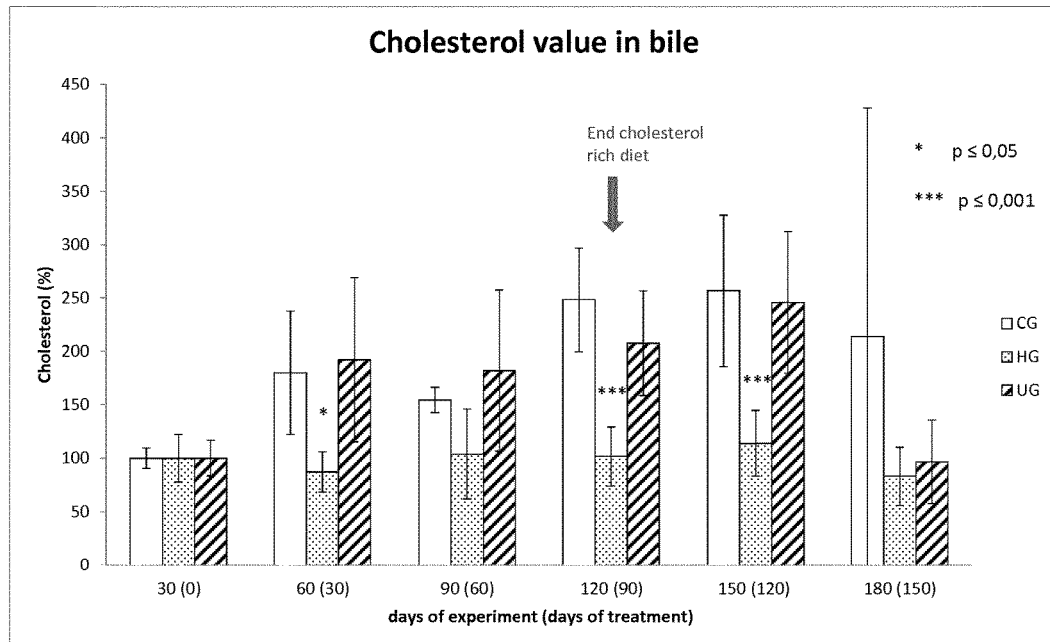

FIG. 2: In vivo testing of a standardized extract; a) graphical representation of the level of cholesterol in the bile over time for the different experimental groups; b) graphical representation of the level of cholesterol in the blood over time for the different experimental groups.

DETAILED DESCRIPTION

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. Nevertheless, where the term comprising is used to refer to the presence of a number of elements or steps this is meant to also include embodiments which are characterized in that they consist only of the recited elements and steps.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The term "standardized extract" as used herein refers to the fact that the extract contains a well-defined concentration of active constituents or marker compounds. More particularly the term "standardized Hh extract" as referred to herein, refers to an extract, such as but not limited to extracts obtainable by the methods described herein, in which the total amount of saponins is between 5% and 18%, and which in addition comprises flavonoids.

The application envisages the use of *Herniaria hirsuta* extracts, more particularly *Herniaria hirsuta* extracts characterized by well-defined concentrations of saponins and the presence of flavonoids in therapeutic methods. Indeed, while therapeutic properties have been ascribed to *Herniaria hirsuta* extracts in the past, the efficacy of these extracts was limited and the effects moreover lacked reproducibility. It has now been found that extracts of *Herniaria hirsuta*, more particularly characterized by well-defined concentrations of saponins and the presence of flavonoids are effective in the prevention and/or treatment of diseases related to the development of stones in the ducts of the digestive tract. More particularly, the diseases envisaged are diseases related to the development of stones in the cystic duct and the common bile, as well as the hepatic or pancreatic ducts.

In particular embodiments, the diseases envisaged include but are not limited to biliary diskinesis, more particularly cholelithiasis, choledocholithiasis and related diseases such as cholangitis, obstructive jaundice, and pancreatitis.

In particular embodiments, the application provides extracts for use in reducing bile cholesterol. More particularly, methods are envisaged whereby administration of the extract ensures a decrease in bile cholesterol of more than 30%, such as 35%, but more particularly 40%, 45% or more than 50%.

The extracts envisaged herein are particularly suitable for the prevention of the diseases mentioned above in subjects at high risk of developing these diseases. Risk factors for developing these diseases include but are not limited to, being female, being age 60 or older, being overweight or obese, being pregnant, eating a high-fat diet and eating a high-cholesterol diet. In particular embodiments, the extracts are envisaged for the prevention and treatment of the diseases listed above in subjects having one or more of these risk factors. In particular, the extracts are envisaged for use in the prevention or treatment of these diseases.

In particular embodiments, it is envisaged that the methods are of particular interest for subjects which are obese and/or on a high-fat or high-cholesterol diet.

The methods envisaged herein involve administering to a mammal, such as a human or a mammal animal, an effective amount of a composition comprising a *Herniaria hirsuta* extract. The dosage of the composition will depend on the concentration of the extract. In particular embodiments, the composition comprises *Herniaria hirsuta* extract material in which the total amount of saponins is between 5% and 18% and which in addition contains flavonoids. It has been found that, where the use of such standardized material is envisaged, the optimal dosage may vary between 0.5 g/day and 10.0 g/day, more particularly between 2.0 g/day and 8.0 g/day, more particularly between 3.0 g/day and 6.0 g/day.

Alternatively, it is envisaged that a *Herniaria hirsuta* extract and more particularly the standardized Hh extract as envisaged herein may be administered at a daily dose between 30 mg/kg body weight and 70 mg/kg body weight, or between 40 mg/kg body weight and 60 mg/kg body weight, or between 45 mg/kg body weight and 55 mg/kg body weight. Dosage treatment may be a single dose schedule or a multiple dose schedule. In particularly the *Herniaria hirsuta* extract and more particularly the standardized Hh extract as envisaged herein may be administered twice a day at a dose between 15 mg/kg body weight and 35 mg/kg body weight, or between 20 mg/kg body weight and 30 mg/kg body weight, or between 22.5 mg/kg body weight and 27.5 mg/kg body weight.

The *Herniaria hirsuta* extracts envisaged herein are characterized by a well-defined concentration of *Herniaria hirsuta* saponins and the presence of *Herniaria hirsuta* flavonoids. Where the concentration of the *Herniaria hirsuta* extract differs from the standard envisaged above, the dosage can be adjusted accordingly by the skilled person. It is envisaged that optimal effects are achieved when the methods encompass the administration of between 3.0 mg and 8.4 mg/kg bodyweight of *Herniaria hirsuta* saponins per day. In particular embodiments it has been found that the amount of *Herniaria hirsuta* flavonoids present in the composition to be administered is between 0.5% and 7%. In further particular embodiments, the amount of flavonoids present in the extract is between 4-5%. Based thereon optimal effects are achieved when the methods encompass the administration of between 0.15-3.5 mg/kg bodyweight of flavonoids per day.

The compositions may take a variety of forms such as pills, candies, lozenges, powders, gels, tablets, beverages, nutritional products and the like.

An "effective amount" of a composition is the amount of said composition, and more particularly of the extract provided herein, required and sufficient to elicit an adequate response in preventing or treating or reducing the intended or targeted medical indication. Such a response may require successive administrations of the composition. The effective amount may further vary depending on the health and physical condition of the individual to be treated, the age of the individual to be treated, the ability of the subject to respond effectively, the nature of the composition (formulation) and other relevant factors. The effective amount further may vary depending on whether it is used in monotherapy or in combination therapy.

In the methods of prevention and treatment envisaged herein the subject may be an adult, child or infant.

In particular embodiments the methods envisaged herein comprise administration of a *Herniaria hirsuta* extract, more particularly the standardized Hh extract envisaged herein, over a prolonged period of time. Typically the time-period extends between 30 days and 3 years. In particular embodiments, the time period is a time period of more than 3 months, most particularly between 4 and 6 months and even more particularly, 4, 5 or 6 months.

The application provides methods for providing standardized *Herniaria hirsuta* extracts, which can be used for the preparation of therapeutic compositions. The methods for producing standardized extract material of *Herniaria hirsuta*, comprise the steps of generating an extract of *Herniaria hirsuta* plant material, determining the amount of *Herniaria hirsuta* saponins and the presence of flavonoids in the extract so obtained and obtaining therefrom *Herniaria hirsuta* extract material with a well-defined concentration of saponins. In particular embodiments, the methods involve generating extract material in which the total amount of *Herniaria hirsuta* saponins is between 5% and 18%. In further particular embodiments, the extract is further characterized in that the total amount of *Herniaria hirsuta* flavonoids is between 0.5% and 7%.

Accordingly, in particular embodiments, methods are provided for producing a *Herniaria hirsuta* extract, more particularly a therapeutically effective *Herniaria hirsuta* extract, which comprise the steps of contacting plant material of *Herniaria hirsuta*, with an extraction fluid so as to extract at least flavonoids and saponins therefrom; determining the amount of *Herniaria hirsuta* saponins and the presence of flavonoids in the extract so obtained; and obtaining therefrom an extract material wherein the total amount of *Herniaria hirsuta* saponins is between 5% and 18%, and wherein *Herniaria hirsuta* flavonoids are present. In further particular embodiments, the methods may further encompass determining the amount of *Herniaria hirsuta* flavonoids in the extract. In yet further embodiments the methods may encompass obtaining an extract material wherein the total amount of *Herniaria hirsuta* flavonoids is between 0.5-7%. In yet further embodiments, the total amount of *Herniaria hirsuta* flavonoids is between 2% and 7%.

The method by which the *Herniaria hirsuta* extract is obtained is not critical. Indeed, it will be clear to the skilled person that extracts comprising at least flavonoids and saponins can be obtained from plant material in different ways. Thus, the plant material can be contacted with different fluids such as but not limited to ethylacetate, ethanol, methanol, acetone and combinations thereof.

The application further provides an optimized but only exemplary method for the generation of a *Herniaria hirsuta* extract suitable for the generation of therapeutic compositions, i.e. devoid of excess compounds which would be toxic and comprising suitable amounts of saponins and flavonoids. More particularly the process comprises the steps of extracting the *Herniaria hirsuta* plant material in boiling water separating the insoluble plant material from the aqueous phase; and concentrating the solute contained in the aqueous phase. The concentrated solute may then be subjected to freeze drying, spray drying, evaporation or ultrafiltration.

As detailed above, the methods for the generation of *Herniaria hirsuta* extract envisaged herein further comprise the step of determining the amount of *Herniaria hirsuta* saponins and the presence of *Herniaria hirsuta* flavonoids in the extract obtained. In further particular embodiments the methods comprise the step of determining the amount *Herniaria hirsuta* saponins and flavonoids in the extract. Suitable methods for determining the amount of saponins and the presence of flavonoids in an extract are known to the skilled person. For instance the extract may be analysed by a chromatographic method such as, but not limited to HPLC. Typically, quantification or identification of components will be performed using standards. More particularly, quantification or identification can be ensured by using a flavonoid and/or a saponin standard. Suitable flavonoid and saponin standards for the determination of *Herniaria hirsuta* flavonoids and saponins are available in the art and include but are not limited to the flavonoid compounds rutin, quercetin or quercitrin and the saponins α-hederacoside C, alpha-hederin, and hederagenin.

In order to obtain a material suitable for the generation of a therapeutic composition, the methods envisaged herein further comprise the step of generating, from one or more *Herniaria hirsuta* extracts so obtained, a *Herniaria hirsuta* extract material with a well-defined concentration of saponins, in which in addition flavonoids are present.

In particular embodiments, the *Herniaria hirsuta* extract material comprises a total amount of saponins between 5% and 20%, and the presence of flavonoids. Thus, in particular embodiments, the methods comprise determining whether the total amount of saponins is between 5% and 20%, and whether flavonoids are present.

In particular embodiments, the *Herniaria hirsuta* extract material comprises a total amount of saponins between 5% and 18% and a total amount of flavonoids between 0.5% and 7%, more particularly between 2% and 7%. Thus, in particular embodiments, the methods comprise determining whether the total amount of saponins is between 5% and 18% and whether the total amount of flavonoids in the extract is between 0.5% and 7%, more particularly between 2% and 5%.

In further embodiments, the methods may comprise mixing different batches of *Herniaria hirsuta* extracts. In particular embodiments, where the total amount of saponins does not correspond to the amount envisaged, the methods may comprise the step of mixing a batch of extract comprising lower concentration with a batch comprising a higher concentration of saponins. In further particular embodiments, the methods comprise determining whether the total amount of saponins is about 9-13%. In further particular embodiments, the methods comprise determining whether, in addition, the total amount of flavonoids is between 0.5-7%. In particular embodiments, the methods comprise determining whether the total amount of saponins is between 9-13% and the total amount of flavonoids is between 4-6%.

In further embodiments, in order to reach the target concentration for the phytochemical constituents one or more batches of *Herniaria hirsuta* extract is mixed with one or more inert excipients (dilution).

The application thus also provides extracts of *Herniaria hirsuta*, which can be used for the generation of compositions suitable for the prevention and treatment of diseases caused by the presence of stones in the secondary ducts of the digestive system. *Herniaria hirsuta* L. (*Caryophyllaceae*), is a plant native to Eurasia and Northern Africa but currently also found in Europe. The extracts of *Herniaria hirsuta* envisaged herein contain saponins as main components, and also comprise flavonoids. More particularly, the extracts of *Herniaria hirsuta* are characterized by the presence of *Herniaria hirsuta* saponins and flavonoids. Indeed, the saponins and flavonoids present therein are characteristic for *Herniaria hirsuta*, such that a *Herniaria hirsuta* extract will differ from an extract of another plant, or even from that of another *Herniaria* species.

In particular embodiments, the standardized *Herniaria hirsuta* extracts envisaged herein are characterized in that the *Herniaria hirsuta* saponins comprised therein include one or more of hydroxymedicagenic acid heptaglycoside and medicagenic acid heptaglycoside.

In further particular embodiments, the standardized *Herniaria hirsuta* extracts envisaged herein are characterized in that they comprise the *Herniaria hirsuta* saponins hydroxymedicagenic acid heptaglycoside and medicagenic acid heptaglycoside.

In particular embodiments, the *Herniaria hirsuta* extracts envisaged herein comprise one or more of quercetine-3-O-(2-O-rhamnosyl)glucuronide, rutine and isorhamnetine-3-O-rutinoside. In further particular embodiments, the extracts comprise quercetine-3-O-(2-O-rhamnosyl)glucuronide, rutine and isorhamnetine-3-O-rutinoside.

In particular embodiments, the *Herniaria hirsuta* extracts as envisaged herein are characterized by having a composition as detailed in Table 1 herein. In further particular embodiments, the extracts are characterized by an HPLC profile as provided in FIG. 1 herein.

In particular embodiments as detailed herein, the *Herniaria hirsuta* extracts envisaged herein are further characterized in that he total amount of saponins is between 3% and 25%, and that flavonoids are present. The application more particularly provides standardized extracts of *Herniaria hirsuta*, characterized in that the total amount of saponins is between 5% and 18%, and that flavonoids are present. In particular embodiments, the total amount of saponins is about 9-13%. Indeed, it has been found that such extracts are particularly suitable to ensure the therapeutic effects disclosed herein.

In addition, in particular embodiments, the extract may be characterized in that the total amount of flavonoids is about 0.5% or more. In particular embodiments, the total amount of flavonoids is about 0.5%. In further particular embodiments, the total amount of flavonoids may be between 1% and 10%, or between 2-7%.

These and other aspects of the invention will become apparent to those skilled in the art as a result of the following examples which are intended as illustrative of the invention and not limitative.

EXAMPLES

1. Preparation of an Extract of *Herniaria hirsuta* Plant Material

For the preparation of a standardized extract the aerial parts of *Herniaria hirsuta* were collected (Oujda, Morocco). The material was air dried. The extract was prepared by the infusion of 80 g of the dried plant material in 4 l boiled water during 30 min with continuous stirring. After filtration the infuse was lyophilized.

Typically, 100 g of plant material yielded about 15 g of lyophilizate.

Quantification of the dry extract was performed by means of the method described below.

2. Development of an HPLC Method for the Simultaneous Determination of Saponins and Flavonoids in *Herniaria hirsuta* Extracts A method was developed for the quality control of the standardized extract by the simultaneous determination of saponins and flavonoids. The method was as follows:

100 mg of the lyophilized extract was accurately weighed in a calibrated flask of 25.0 ml, filled up with methanol (Fisher Scientific, Hampton, N.H., USA) 50% (v/v) and ultrasonicated during 20 min. After cooling down, the resulting sample solutions were filtered through a 0.45 µm syringe filter (Grace, Deerfield, USA). For the subsequent HPLC analysis, 50 µl of the sample solution was injected on an Apollo C18 column (4.6 mm×250 mm, 5 µm) (Grace, Deerfield, USA). A flow rate of 1 ml/min was chosen and the following gradient was used: mobile phase A=$H_2O$+0.05% FA (Acros, Geel, Belgium), B=methanol (Fisher Scientific, Hampton, N.H., USA)+0.05% FA (Acros, Geel, Belgium); gradient: start at 5% B—stay at 5% B during 5 min—from 5% to 100% B in 55 min—stay at 100% during 2 min—from 100% to 5% B in 1 min—stay at 5% B during 2 min.

An exemplary run is provided in FIG. 1.

The flavonoid content was determined using rutin (Extrasynthese, Genay Cedex, France and Sigma, Bornem, Belgium) as external standard while the saponin content was expressed as α-hederacoside C (Extrasynthese, Genay Cedex, France and Roth, Karlsruhe, Germany).

The method was validated according to the ICH guidelines. The calibration model, range, linearity, precision, accuracy and specificity were investigated.

The calibration model of the two selected standards was investigated. Therefore five concentration levels of both rutin (1.28—489.50 µg/ml) (Extrasynthese, Genay Cedex, France and Sigma, Bornem, Belgium) and α-hederacoside C (19.52—780.61 µg/ml) (Extrasynthese, Genay Cedex, France and Roth, Karlsruhe, Germany) were prepared. All solutions were analyzed twice. The regression line was constructed, the equation was generated and the correlation coefficient calculated. The slope and intercept were investigated with a Student t-test. The residuals were graphically evaluated. Also an ANOVA lack of fit test was performed.

For the repeatability of the injection, one sample was analyzed 6 times (system precision). Also the precision of the method, i.e. the repeatability and the intermediate precision were investigated. Therefore six independently prepared samples (100%; 100 mg) were analyzed according to the above described method. The procedure was repeated on three different days and on three concentration levels (50%-100%-150%). A solution of both the standards, used to determine the amount of flavonoids and saponins was freshly prepared each day and analyzed twice, using the same HPLC method. The mean, the standard deviation and the relative standard deviation (RSD %) were calculated for each day and each concentration level. The overall mean, overall standard deviation and overall RSD % were calculated for the three days and also for the three different concentration levels. This was done for the individual flavonoids and saponins and for their total amounts. The repeatability and intermediate precision were evaluated by an ANOVA single factor test. For the repeatability, the within mean squares were used to calculate the standard deviation and RSD %. For the intermediate precision, the standard deviation was calculated using the following formula: ((MSbetween−MSwithin)/n+MSwithin) 0.5). Before performing the ANOVA single factor, a Cochran test was done.

To investigate the accuracy of the method, a recovery experiment was performed. To 50% of the infusion of *H. hirsuta* a known amount of rutin (Extrasynthese, Genay Cedex, France and Sigma, Bornem, Belgium) or α-hederacoside C (Extrasynthese, Genay Cedex, France and Roth, Karlsruhe, Germany) was added until a total concentration of 100% of either rutin (Extrasynthese, Genay Cedex, France and Sigma, Bornem, Belgium) or the saponins. For both compounds. The samples were prepared in triplicate according to the described procedure.

An overview of the amount of flavonoids and the amount of saponins present in the extract obtained is provided in Table 1 below.

| Compound | Identification | concentration | Molecular weight |
|---|---|---|---|
| 1 | Caffeic acid derivative | Not quantified | Not determined |
| 2 | quercetine-3-O-(2-O-rhamnosyl)glucuronide | 2.03% | 624 |
| 3 | Flavonoid | 0.26% | Not determined |
| 4 | Flavonoid | 0.37% | Not determined |
| 5 | Rutine | 0.93% | 610 |
| 6 | Isorhamnetine-3-O-rutinoside | 0.67% | 624 |
| 7 | Saponin: hydroxymedicagenic acid heptaglucoside | 3.2% | 1558 |
| 8 | Saponin | 1.4% | 1104 |
| 9 | Saponin: medicagenic acid heptaglycoside | 7.7% | 1542 |

The concentration of the total amount of flavonoids and saponins in the extract was determined as being 4.3%±1.85% and 12.28%±5.83% (mean±RSD %), respectively.

3. In Vivo Evaluation of the Therapeutic Effect of the *Herniaria hirsuta* Extract 3.1. Experimental Protocol for the In Vivo Evaluation All experiments were approved by the Ethical Committee of the University of Rabat, Morocco. 21 dogs (14.5±4.9 kg) were collected for the experiment; temperature in the animalarium ranged between 16-35° C. on a natural light-dark cycle. Dogs used in the experiment were divided into one group of control dogs (CG, seven dogs), one group of dogs treated with UDCA (UG, seven dogs) and one group of dogs treated with an extract of *H. hirsuta* obtained in Example 2 (HG, seven dogs). Each dog was caged individually and was subjected to an acclimatization period of 15 days in the new environment before starting the experiment. During this period all dogs received an anti-parasitic treatment. Subsequently all dogs were daily fed 200 g horse meat containing 50% sheep fat during 120 days, after which all dogs were daily fed 200 g horse meat without sheep fat till the end of the experiment (day 180). At day 30 of the experiment treatment of the different groups started. While CG dogs received no additional treatment, UG dogs received two times a day a dose of 7.35 mg/kg body weight UDCA and HG dogs received two times a day a dose of 48.5 mg/kg body weight of the herbal extract (based on Settaf et al. 2000) till the end of the experiment (day 180). UDCA or the herbal extract were mixed with a small quantity of meat making sure the entire treatment dose was administered to each dog. A bile and blood sample of each dog was collected every 30 days, after which the concentration of cholesterol was determined. For the collection of the bile the following surgical method was used: All dogs received marbofloxacin 2% (1 mg/kg body weight), acepromazin (0.05 mg/kg body weight, IM), atropine (0.04 mg/kg body weight, IM) and tolfenamic acid (4 mg/kg body weight, IM) before surgery. Induction of anesthesia was done depending on the weight of the dogs with sodium thiopental (15 mg/kg body weight, IV) or xylazine (0.5 mg/kg body weight, IV) combined with ketamin (15 mg/kg body weight, IV). For the maintenance of sedation isoflurane (1 l/min) (xylazine, ketamine) was used. During surgery all dogs received artificial breathing through a tracheal tube. Each surgery bile was collected by puncturing the gallbladder. Bile and blood samples were immediately stored at −20° C. after which quantification of the cholesterol in both bile and blood was performed by an enzymatic method (DiaSys Cholesterol FS).

After each surgical procedure each dog received marbofloxacin 2% (1 mg/kg body weight) during 4 days. The body weight of all dogs was monitored during the entire experiment.

3.2. Statistical Analysis

Data are expressed as mean±SEM. Data were analyzed using one way analysis of variance (ANOVA), followed by the Bonferroni test or Kruskal-Wallis analysis and Dunnett T3. $P \leq 0.05$ was considered significant.

3.3. Ames Test

An Ames test was performed according to the OECD-guidelines (Abdillahi et al., 2012). The standardized extract was tested on 5 *Salmonella typhimurium* strains (TA 1535, TA 100, TA 98, TA 1537, TA 102), whether or not in the presence of metabolising S9-fraction. Six concentrations of the extract were tested (5 mg/plate, 1.5 mg/plate, 0.5 mg/plate, 0.15 mg/plate, 0.05 mg/plate, 0.015 mg/plate) and depending on the bacterial strain and the absence and presence of the S9-fraction different positive controls were included in the test. The respective positive controls for TA 1535 were sodium azide (50 μg/ml) and 2-aminoanthracene (25 μg/ml), for TA 100 sodium azide (50 μg/ml) and 2-aminoanthracene (10 μg/ml), for TA 98 4-nitroquinoline-1-oxide (2 μg/ml) and 2-aminoanthracene (25 μg/ml), for TA 1537 9-aminoacridine (500 μg/ml) in both situations and for TA 102 4-nitroquinoline-1-oxide (10 μg/ml) and 2-aminoanthracene (25 μg/ml). Each concentration was tested in triplicate, while negative controls were performed in quadruplicate. Results are expressed as mean number of revertants±SEM.

3.4. Results

The level of cholesterol in the bile was determined for all dogs starting at day 30 of the experiment and with time intervals of 30 days and is depicted in FIG. 2A. It was observed that the control group (CG) and the group that received UDCA (UG) showed an increase in bile cholesterol over time, until day 120 (90 days of treatment) when the cholesterol-rich diet was stopped. However, the bile cholesterol values of the group which received the standardized extract of *H. hirsuta* remained at the starting levels in spite of the continuous administration of a cholesterol-rich diet. Although a minor difference ($p \leq 0.05$) was observed between CG and HG after 30 days of treatment with the extract, this dissimilarity between CG and HG was more profound after 90 days of treatment ($p \leq 0.001$). Even 30 days after discontinuation of the cholesterol-rich diet a significant difference ($p \leq 0.001$) remained between the untreated group and the group which received the standardized extract of *Herniaria hirsuta*. At 150 days of treatment a large standard deviation could be observed in CG, due to the bile cholesterol values of one dog. However, since this value was not marked as an extreme outlier by statistical analysis it was not excluded. Also, elimination of this value did not cause any profound difference in the statistical results after 150 days of treatment, as all three groups remained statistically equal. At any time-point no statistical difference could be observed between CG and UG.

The decrease in values for cholesterol in blood is depicted in FIG. 2B. Here also a tendency to decrease over time was observed, albeit less significant. No statistically significant difference could be observed for CG and UG between the different time-points. For HG a difference could be observed which started after 90 days of treatment with the standardized extract and remained till the end of the experiment. Despite this difference over time, all three groups (CG, UG and HG) remained statistically equal for cholesterol values in blood at the different time-points. Concerning the body weight of the dogs, all groups were statistically equal and dogs gained or lost no body weight over time.

The results obtained for the Ames test showed no dose-response relationship or a doubling of the amount of revertants in comparison with the negative control.

CONCLUSION

In order to demonstrate the effect of a standardized extract containing a defined amount of flavonoids and saponins as main components on the treatment and prevention of Gallstones, the in vivo tests were carried out under high fat diet conditions, which increase the bile cholesterol level and favours the bile mud and gallstone formation. It is demonstrated that even in such unfavourable and unhealthy conditions, the standardized Hh extract will prevent the increase of bile cholesterol and therefore prevent bile mud and gallstone formation.

This is in contrast to previous *Herniaria* extracts which have only been demonstrated to decrease the bile cholesterol by 28-30%, similar to UDCA effect (Settaf et al., 2000, Biologie & Santé 1(1), 44-49) under normal diet conditions. This percentage of decrease under normal diet conditions cannot imply that the claimed effect will be produced in such high fat diet and unfavourable conditions.

Prolonged use of a standardized *Herniaria hirsuta* extract results in a cholesterol-lowering effect in the bile but not in blood of dogs when maintaining a cholesterol-rich diet. Since this pharmacological effect prevents the formation of gallstones and can contribute to solving existing gallstones, a standardized preparation of *H. hirsuta* may have a positive effect in the treatment of gallstones in human patients.

The invention claimed is:

1. A method of treating or reducing the incidence of cholelithiasis or choledocholithiasis in a subject comprising administering to the subject a *Herniaria hirsuta* extract comprising one or more *Herniaria hirsuta* flavonoids and one or more *Herniaria hirsuta* saponins, wherein the extract is administered in an amount effective to treat or reduce the incidence of cholelithiasis or choledocholithiasis in a subject.

2. The method according to claim 1, wherein the method lowers bile cholesterol.

3. The method according to claim 1, wherein the *Herniaria hirsuta* extract comprises one or more of hydroxymedicagenic acid heptaglycoside and medicagenic acid heptaglycoside.

4. The method according to claim 1, wherein the *Herniaria hirsuta* flavonoids comprise one or more of quercetine-3-O-(2-O-rhamnosyl)glucuronide, rutine and isorhamnetine-3-O-rutinoside.

5. The method of claim 1, wherein the extract is administered to the subject at a dose of between 3.6 mg and 8.4 mg/kg bodyweight of *Herniaria hirsuta* saponins per day.

6. A method of treating or reducing the incidence of a disease associated with stones in the duct of the digestive system in a subject comprising administering to the subject a standardized *Herniaria hirsuta* extract comprising one or more *Herniaria hirsuta* flavonoids and one or more *Herniaria hirsuta* saponins, wherein the total amount of flavonoids is between 0.5% and 7% and the total amount of saponins is between 5% and 18%, and the extract is administered in an amount effective to treat or reduce the incidence of the disease.

7. The method according to claim 6, wherein the standardized *Herniaria hirsuta* extract comprises one or more of hydroxymedicagenic acid heptaglycoside and medicagenic acid heptaglycoside.

8. The method according to claim 6, wherein the *Herniaria hirsuta* flavonoids comprise one or more of quercetine-3-O-(2-O-rhamnosyl)glucuronide, rutine and isorhamnetine-3-O-rutinoside.

9. The method according to claim 6, wherein the disease is cholelithiasis or choledocholithiasis.

10. The method according to claim 9, wherein said extract is administered at a dosage between 0.5 g/day and 10.0 g/day.

11. A method of treating or reducing the incidence of cholelithiasis or choledocholithiasis or a disease associated with stones in the duct of the digestive system in a subject comprising administering to the subject the standardized *Herniaria hirsuta* extract in an amount effective to treat or reduce the incidence of the disease said extract was produced by the steps of: a) contacting plant material of *Herniaria hirsuta*, with an extraction fluid so as to extract flavonoids and saponins therefrom; b) determining the amount of *Herniaria hirsuta* saponins and the presence of *Herniaria hirsuta* flavonoids in the extract so obtained; and c) obtaining therefrom an extract material wherein the total amount of *Herniaria hirsute* saponins is between 5% and 18%, and wherein the total amount of *Herniaria hirsuta* flavonoids is between 0.5% and 7%.

12. The method according to claim 11, wherein step (c) comprises mixing different batches of *Herniaria hirsuta* extracts, or mixing with one or more inert excipients.

\* \* \* \* \*